(12) United States Patent  
Larroque-Lahitette et al.

(10) Patent No.: US 8,936,625 B2  
(45) Date of Patent: Jan. 20, 2015

(54) DEVICE FOR FIXING A BONY STRUCTURE TO A SUPPORT MEMBER

(71) Applicant: Zimmer Spine, Bordeaux (FR)

(72) Inventors: Gilles Larroque-Lahitette, Lagor (FR); Georges Legallois, Bordeaux (FR)

(73) Assignee: Zimmer Spine, Bordeaux (FR)

( * ) Notice: Subject to any disclaimer, the term of this patent is extended or adjusted under 35 U.S.C. 154(b) by 13 days.

(21) Appl. No.: 13/906,880

(22) Filed: May 31, 2013

(65) Prior Publication Data

US 2013/0325070 A1    Dec. 5, 2013

(30) Foreign Application Priority Data

Jun. 1, 2012   (EP) ..................................... 12305614

(51) Int. Cl.
 *A61B 17/70*   (2006.01)

(52) U.S. Cl.
 CPC .......... *A61B 17/7047* (2013.01); *A61B 17/7032* (2013.01); *A61B 17/7053* (2013.01); *A61B 17/707* (2013.01); *A61B 17/7002* (2013.01)
 USPC ........................................... 606/277; 606/278

(58) Field of Classification Search
 CPC ........................... A61B 17/7049; A61B 17/705
 USPC ...................... 606/246–279, 74; 16/357, 253; 403/191, 234, 235
 See application file for complete search history.

(56) References Cited

U.S. PATENT DOCUMENTS

| 2,167,489 | A | * | 7/1939 | Renga | 16/357 |
|---|---|---|---|---|---|
| 2,249,403 | A | * | 7/1941 | Stollsteimer | 248/240.3 |
| 2,385,738 | A | * | 9/1945 | Stanton | 312/270.3 |
| 2,550,040 | A | * | 4/1951 | Clar | 165/63 |
| 2,625,426 | A | * | 1/1953 | Weymouth | 296/97.11 |
| 2,638,629 | A | * | 5/1953 | Heintz | 425/25 |
| 2,765,207 | A | * | 10/1956 | Moore | 312/248 |
| 2,975,847 | A | * | 3/1961 | Feucht | 173/60 |
| 3,038,184 | A | * | 6/1962 | Fitzpatrick | 12/117.4 |
| 3,121,385 | A | * | 2/1964 | Blackburn et al. | 99/374 |
| 4,611,582 | A | * | 9/1986 | Duff | 606/258 |
| 5,274,902 | A | * | 1/1994 | Rowley | 29/525.04 |
| 5,356,412 | A | * | 10/1994 | Golds et al. | 606/74 |
| 5,496,318 | A | * | 3/1996 | Howland et al. | 606/249 |
| 5,527,314 | A | * | 6/1996 | Brumfield et al. | 606/278 |
| 5,534,002 | A | * | 7/1996 | Brumfield et al. | 606/278 |
| 5,609,592 | A | * | 3/1997 | Brumfield et al. | 606/250 |

(Continued)

FOREIGN PATENT DOCUMENTS

EP    2052689 A1   4/2009
FR    2929100 A1   10/2009

*Primary Examiner* — Eduardo C Robert
*Assistant Examiner* — Stuart S Bray
(74) *Attorney, Agent, or Firm* — Seager, Tufte & Wickhem, LLC (57) ABSTRACT

A device for fixing a bony structure to a support member. The device includes a main body with first and second members, the second member being movable in rotation with respect to the first member, around a first axis. A flexible member passes between the members and forms a loop around a bony structure. A clamping mechanism moves the first and second members into a clamping position. A support member and the flexible member are secured between the members in the clamping position. The first axis is movable in translation along a first direction and the second member is movable in translation along the first direction. The clamping mechanism cooperates with the first and second members to move the second member in translation in the first direction.

14 Claims, 4 Drawing Sheets

(56) References Cited

U.S. PATENT DOCUMENTS

| | | | |
|---|---|---|---|
| 5,609,634 A * | 3/1997 | Voydeville | 623/13.11 |
| 5,653,711 A * | 8/1997 | Hayano et al. | 606/74 |
| 5,669,107 A * | 9/1997 | Carlsen et al. | 16/348 |
| 5,738,179 A * | 4/1998 | Matsui | 180/69.21 |
| 6,086,590 A * | 7/2000 | Margulies et al. | 606/263 |
| 6,243,920 B1 * | 6/2001 | Sauve | 16/361 |
| 6,292,981 B1 * | 9/2001 | Ford et al. | 16/357 |
| 6,387,097 B1 * | 5/2002 | Alby | 606/277 |
| 6,401,299 B1 * | 6/2002 | Schwarz | 16/335 |
| 6,430,776 B1 * | 8/2002 | Tan et al. | 16/325 |
| 6,802,845 B2 * | 10/2004 | Shirado et al. | 606/324 |
| 6,862,858 B2 * | 3/2005 | Salice | 52/584.1 |
| 7,033,358 B2 * | 4/2006 | Taylor et al. | 606/277 |
| 7,131,972 B2 * | 11/2006 | Mazda et al. | 606/250 |
| 7,481,828 B2 * | 1/2009 | Mazda et al. | 606/263 |
| 7,585,299 B2 * | 9/2009 | Rezach | 606/60 |
| 7,666,210 B2 * | 2/2010 | Franck et al. | 606/250 |
| 7,699,874 B2 * | 4/2010 | Young | 606/270 |
| 7,722,645 B2 * | 5/2010 | Bryan | 606/246 |
| 7,771,474 B2 * | 8/2010 | Cordaro | 623/17.11 |
| 7,857,836 B2 * | 12/2010 | Huebner et al. | 606/280 |
| 7,887,537 B2 * | 2/2011 | Ferrante et al. | 606/59 |
| 7,918,876 B2 * | 4/2011 | Mueller et al. | 606/251 |
| 7,959,654 B2 * | 6/2011 | Mazda et al. | 606/263 |
| 8,172,843 B2 * | 5/2012 | Baccelli et al. | 606/74 |
| 8,192,467 B2 * | 6/2012 | Felix et al. | 606/250 |
| 8,226,689 B2 * | 7/2012 | Jones et al. | 606/250 |
| 8,262,700 B2 * | 9/2012 | Cho et al. | 606/250 |
| 8,277,451 B2 * | 10/2012 | Fernandez | 606/74 |
| 8,313,513 B2 * | 11/2012 | Beger et al. | 606/249 |
| 8,468,655 B2 * | 6/2013 | Borkgren et al. | 16/348 |
| 8,568,453 B2 * | 10/2013 | Abdou | 606/248 |
| 8,747,405 B2 * | 6/2014 | Belliard | 606/74 |
| 2002/0165503 A1 * | 11/2002 | Morris et al. | 604/250 |
| 2003/0109882 A1 * | 6/2003 | Shirado et al. | 606/61 |
| 2003/0114851 A1 * | 6/2003 | Truckai et al. | 606/51 |
| 2004/0064140 A1 * | 4/2004 | Taylor et al. | 606/61 |
| 2004/0260285 A1 * | 12/2004 | Steib et al. | 606/61 |
| 2005/0113831 A1 * | 5/2005 | Franck et al. | 606/61 |
| 2006/0135958 A1 * | 6/2006 | Marissen et al. | 606/74 |
| 2006/0213373 A1 * | 9/2006 | Fernandez et al. | 99/349 |
| 2006/0271055 A1 * | 11/2006 | Thramann | 606/74 |
| 2007/0000393 A1 * | 1/2007 | Lam | 99/372 |
| 2007/0006740 A1 * | 1/2007 | Lam | 99/372 |
| 2007/0055251 A1 * | 3/2007 | Huebner et al. | 606/69 |
| 2007/0100339 A1 * | 5/2007 | Clement et al. | 606/61 |
| 2007/0161994 A1 | 7/2007 | Lowery et al. | |
| 2007/0187450 A1 * | 8/2007 | Chang | 227/129 |
| 2007/0260251 A1 * | 11/2007 | Weier et al. | 606/74 |
| 2007/0265630 A1 * | 11/2007 | Marissen et al. | 606/74 |
| 2008/0195150 A1 * | 8/2008 | Bishop | 606/246 |
| 2009/0082820 A1 * | 3/2009 | Fielding et al. | 606/326 |
| 2009/0093848 A1 * | 4/2009 | Neary et al. | 606/277 |
| 2009/0099604 A1 * | 4/2009 | Cho et al. | 606/250 |
| 2009/0138048 A1 * | 5/2009 | Baccelli et al. | 606/263 |
| 2009/0326588 A1 * | 12/2009 | Felix et al. | 606/277 |
| 2010/0076493 A1 * | 3/2010 | Fauth et al. | 606/279 |
| 2011/0015679 A1 | 1/2011 | Fiere et al. | |
| 2011/0183280 A1 * | 7/2011 | Cosse et al. | 433/13 |
| 2011/0190771 A1 * | 8/2011 | Fernandez | 606/74 |
| 2012/0059377 A1 * | 3/2012 | Belliard | 606/74 |
| 2012/0130373 A1 * | 5/2012 | Larroque-Lahitette | 606/74 |
| 2012/0157998 A1 * | 6/2012 | Belliard | 606/74 |
| 2012/0245641 A1 * | 9/2012 | Mekhail et al. | 606/279 |
| 2012/0303065 A1 * | 11/2012 | Larroque-Lahitette et al. | 606/277 |
| 2013/0231704 A1 * | 9/2013 | Larroque-Lahitette | 606/277 |

* cited by examiner

DEVICE FOR FIXING A BONY STRUCTURE TO A SUPPORT MEMBER

CROSS-REFERENCE TO RELATED APPLICATIONS

This application claims priority to EP12305614.5, filed on Jun. 1, 2012, the entire disclosure of which is incorporated herein by reference.

FIELD OF THE INVENTION

The present disclosure generally relates to a device for fixing a bony structure to a support member, to a system comprising such a device and to a method using it. Such a device may be helpful for holding a bone (e.g. a vertebra) and a support member (e.g. a rod) in a desired configuration. In particular, the present disclosure relates to a system and method for stabilizing at least two vertebrae.

BACKGROUND OF THE INVENTION

One field of application for the invention is holding together a bone and a support member in a desired relative position, while allowing in some cases a limited amount of relative movement, for example to aid in healing of breaks or to correct bony structure deficiencies and abnormalities. In particular, sufferers of abnormal spine curvature or other spine deficiencies may benefit from the invention.

The spine is formed of superposed vertebrae, normally aligned along a vertebral axis, from the lumbar vertebrae to the cervical vertebrae, each having an anterior part: the vertebral body, and a posterior part: the vertebral arch (or neural arch), the anterior and posterior part enclosing the vertebral foramen. Each vertebral arch is formed by a pair of pedicles and a pair of laminae, with transverse processes and/or a spinous process (or neural spine) projecting therefrom. The transverse processes and the spinous process project opposite to the vertebral foramen.

When the vertebrae are articulated with each other, the vertebral bodies form a strong pillar for the support of the head and trunk. In between every pair of vertebral bodies, there is an intervertebral disc.

When the spine of a person has abnormal curvature (e.g. scoliosis) or other deficiencies (e.g. a damaged intervertebral disc), the vertebrae are typically too close together, too far apart or otherwise misaligned, and there is a need to stabilize the vertebrae in a correct position relative to one another. Mainly, there is either a need to compress the vertebrae (i.e. to bring and hold them closer together) or a need to distract the vertebrae (i.e. to move and keep them away from each other).

Devices known in the art for holding vertebrae relative to one another typically include one or more rods that are held by devices attached to the vertebrae by means of screws, hooks, or flexible ligatures. One such device is described in patent document EP2052689A1. This known device comprises a holding body having a receiving portion for receiving the rod and an engagement portion, a closure member for engagement with the engagement portion of the holding body to secure the rod within said receiving portion, and an anchor member for anchoring the holding body to the bony structure of a vertebra.

In the device of EP2052689A1, to create a connection, the receiving portion of the holding body has to be sized to the gauge of the rod used. Since, depending on the specific intervention and patient, a variety of different rod gauges may be required, different holding bodies adapted to accommodate each specific rod gauge need to be provided.

While known devices have proven effective, further improvements would be beneficial.

SUMMARY OF THE INVENTION

Described is a fixing device for fixing a bony structure to a support member. This fixing device comprises:
 a main body comprising first and second members defining between them a first passage configured for receiving the support member, the second member being pivotable with respect to the first member, around a first axis, and
 a clamping mechanism engaging the main body and being configured to move the first and second members towards each other for clamping the support member therebetween.

In an exemplary fixing device, the first axis is movable in translation along a first direction so that the second member is movable in translation along the first direction, with respect to the first member. Such freedom of movement in translation allows the size of the first passage to be adjusted to the gauge of the support member to be used. Proper clamping of a variety of support members having different gauges can thus be obtained.

In certain embodiments, the clamping mechanism engages with the first and second members and is configured to move the second member in translation along the first direction, so as to narrow the first passage. Accordingly, the size of the first passage can be narrowed to the gauge of the support member to be used, by means of the clamping mechanism.

Configurations of the device that allow for the intraoperative adjustment of the first passage of the device that receives the support member can have the advantage of being adjustable to a variety of support members having different gauges, while being made of a limited number of parts, which makes the device simpler to produce and easier to handle.

In certain embodiments, the fixing device is adapted to receive a flexible member within the first passage, in a direction transverse to a longitudinal axis of the first passage.

The fixing device may be adapted to clamp the flexible member between at least one of the first and second members and the support member, when a support member is disposed within the first passage. In this case, the flexible member and the support member can be simultaneously clamped, i.e. the flexible member and the support member can be simultaneously held in position with respect to the fixing device.

At least one of the first and second members may be provided with at least one through opening, said through opening being in communication with the first passage and being configured to guide the flexible member therethrough.

In certain embodiments, the clamping mechanism comprises a clamping member which is configured to cooperate with the first and second members so as to exert a force on the second member, the force having a component along the first direction.

In certain embodiments, the resultant force exerted by the clamping member on the second member is oriented substantially along the first direction, which improves the clamping efficiency.

A variety of clamping mechanisms that cause the flexible member and support member to remain in a fixed position can be utilized. For example, a single clamping mechanism can be used to hold the flexible member and support member in a fixed position, or two or more separate clamping mechanisms can be used to hold the flexible member and support member in a fixed position individually.

In certain embodiments, the clamping member is a screw with a screw head and a shank, the shank being threadably engaged with the first member and the screw head being configured to exert said force on the second member when the screw is tightened (e.g. when it is screwed into the first member). Using a screw as the clamping member is one embodiment which allows the physician to (finely) adjust the clamping force to the needs. In particular, the physician (or other operative) may lock, unlock, move and/or remove the fixing device, merely by screwing or unscrewing the screw.

The fixing device can be preloaded onto a support member with the clamping mechanism partially tightened with final tightening occurring after the physician has the flexible member and support member in its desired position.

In certain embodiments, the screw head defines a first sloped or curved surface and the second member defines, on its outside face, a second sloped or curved surface. The force exerted by the screw onto the second member is exerted through those first and second surfaces when the screw head is tightened. The first sloped or curved surface may be symmetrical around the rotational axis of the screw. It may be, for instance, a circular part of a spherical (or substantially spherical), convex or conical surface of the screw head.

In certain embodiments, the second member is provided with an oblong opening through which the screw shank passes. The longitudinal direction of that oblong opening may be substantially perpendicular to the screw axis and/or to the first axis A.

In certain embodiments, the second member has an inside face defining an abutment for engagement against the support member. This abutment pushes the support member towards the first member when the second member is moved in translation in the first direction. The shape of the abutment is configured to transmit force to support members of different gauges in the best possible way. For example, the outline of the abutment, in a section plane perpendicular to the first axis, may be concave towards the support member. For instance, the abutment may be a groove, the support member being engaged in that groove.

In certain embodiments, a pivoting mechanism is provided between the first and second members, the pivoting mechanism comprising a pivot shaft being received in an oblong opening provided in at least one of the first and second members.

In certain embodiments, one of the first and second members is provided with a pivot shaft extending along the first axis, and the other one of the first and second members is provided with at least one oblong opening (i.e. an opening having an oblong cross-section) through which the pivot shaft passes, the oblong opening having a longitudinal direction substantially parallel to the first direction. The cooperation between the pivot shaft and the oblong opening is a simple and safe solution for the first and second members to move both in translation and rotation with respect to each other. In cross-section, the oblong opening may have an open outline, i.e. an outline with a gap, or a close outline. When the oblong opening has an open outline, the pivot shaft may be inserted into or taken out of the oblong opening sideways, through the gap of the open outline of the opening. The oblong opening may be open in its longitudinal direction, i.e. the gap of the open outline of the opening may be provided along the longitudinal direction of the groove.

In certain embodiments, the pivot shaft is a one-piece shaft extending through the first and second members. This one-piece shaft may be fixedly linked to the first or second member by friction, welding, swaging, crimping, pressing, clamping or any other appropriate solution.

The pivot shaft may also be defined by two pins protruding from one member, on opposite sides thereof, and extending through the oblong openings of the other member.

Also described is a system comprising at least one support member and at least one fixing device, as described above, for fixing a bony structure to the support member.

The support member may be rigid or not. Typically, the support member is a rod or equivalent. The cross-section of the support member may have different shapes. For instance, it may be round, flat or polygonal. The support member may be provided in a variety of gauges (e.g. different widths or diameters) that can be available to a physician for surgery, thus providing the physician with the ability to select an appropriate support member for the patient from a set of available sizes. In particular, the system may comprise a set of support members of different sizes and at least one fixing device.

The system may further comprise a flexible member passing through the first passage, between the support member and said first and/or second member, the flexible member extending outside or beyond the main body for attachment to the bony structure. In particular, the flexible member may form a loop around the bony structure.

The flexible member may be made of any suitable material that is flexible such as a band, wire, ligament, or cord. For instance, the flexible member may be made of a metal, a polymeric material or a combination thereof.

such a system may be a system for stabilizing at least two vertebrae, which comprises: a first fixing device configured to be fastened to a first vertebra, a second fixing device configured to be fastened to a second vertebra, and a support member for connecting the first and second devices together, thereby providing stabilization between the first and second vertebrae; and wherein at least the first fixing device is a device as described above.

The second fixing device may be similar to or different from the first fixing device.

The stabilization system described herein may be used for providing "static stabilization" or "dynamic stabilization" between the vertebrae. Static stabilization typically refers to holding together the vertebrae in a particular relative position, while minimizing movement between the vertebrae, whereas dynamic stabilization typically refers to holding together the vertebrae in a particular relative position, while allowing a limited amount of relative movement between the vertebrae. For dynamic stabilization, the support member and/or the flexible member may have elastic properties.

As explained above, a variety of support members with different gauges (e.g., with different diameters in case of round section rods) may be used with the same fixing device. Different gauges may be needed to treat different pathologies or portions of the bony structure of the spine (e.g., cervical, thoracic, lumbar, sacral regions). Accordingly, the system may include several support members, of different gauges (or different shapes), and at least one fixing device. The gauge of the support member to be used is then chosen by the physician (or other operative), depending on the specific intervention and patient.

Also described is a method for connecting a bony structure to a support member, comprising the steps of: providing a support member and a fixing device as defined above; passing said loop around the bony structure and applying a force to (e.g., tensioning) said loop to change the position of the bony structure, and impeding movement of the bony structure relative to the support member by fixing the position of the flexible member and support member relative to the fixing device, e.g. by clamping the flexible member and the support member between the first and second members.

Such a method may be used for stabilizing at least two vertebrae. In this case, it comprises the steps of: providing a system as described above; fixing the first fixing device to a first vertebra, by passing said loop around a bony part of the vertebra and tensioning said loop; fixing the second fixing device to a second vertebra; and impeding relative movement between the first and second fixing devices by connecting each of them to the support member, relative movement between the first vertebra and the support member being impeded by fixing the position of the flexible member and support member relative to the first fixing device.

These methods have the advantages derived from using a fixing device or a stabilization system according to the present disclosure.

In particular, the physician (or other operative) may be provided with a system comprising one or several fixing devices as described above, and several support members (e.g., several rods) of different gauges. Since the physician is able to accommodate any of the different support members from the set in the fixing device(s), the physician can freely select one appropriate support member (with a particular gauge) without worrying about the compatibility between the selected support member and the fixing device(s). In other terms, regardless of the support member being selected, the physician can use the same type of fixing device. Accordingly, the physician does not waste time in choosing the fixing device. In addition, the physician needs to acquaint himself with the handling and use of one type of fixing device only.

Selection of the appropriate support member may be done depending, e.g., on the pathology or the type of bony structure to be treated.

Such methods may be used for correcting abnormal spine curvature (e.g., scoliosis) or other spine deficiencies (e.g., a damaged intervertebral disc) by compressing or distracting vertebrae.

Other features and advantages of the invention will become apparent from the following detailed description, taken in conjunction with the accompanying drawings, which illustrate, by way of example, some principles of the invention.

BRIEF DESCRIPTION OF THE DRAWINGS

In the drawings, like reference signs generally refer to the same parts throughout the different views. Moreover, parts belonging to different embodiments but having analogous functions are given like reference numbers incremented by 100, 200, etc.

The drawings are not necessarily to scale, emphasis instead generally being placed upon illustrating the principles of the invention.

DETAILED DESCRIPTION

In the following detailed description, it is referred to the accompanying drawings showing examples of fixing devices and stabilization systems. It is intended that these examples be considered as illustrative only, the scope of the invention not being limited to these examples.

Figure 7:
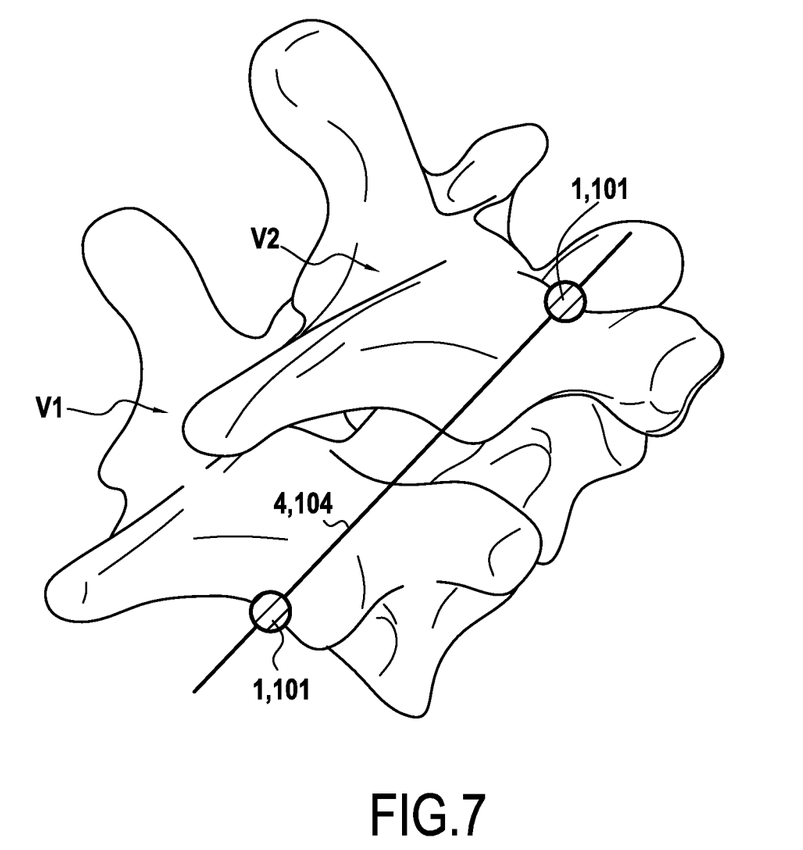
FIG. 7 is a diagrammatic view showing an example of a stabilization system in place on two vertebrae.

A first example of fixing device 1 is shown in FIGS. 1 to 4. This device 1 is for fixing a support member, such as a rod 4 (see FIGS. 2-4), to a bony structure. The bony structure may be, for instance, a vertebra V1 or V2, as shown in FIG. 7.

The rod 4 is an example of support member according to the present disclosure. Here, the rod 4 is rigid and has a circular cross-section. It may be made of biocompatible metallic material.

The fixing device 1 may be made of biocompatible metallic material. It comprises a main body 2 forming a clamp. The main body 2 comprises a first member 13 and a second member 23 linked to the first member 13 over a hinge of axis A. In the figures, the first and second members 13, 23 are, respectively, the lower and upper portions of the main body 2. The rod 4 extends substantially parallel to axis A.

The hinge comprises a pin or shaft 10 passing thought the first and second members 13, 23. When the first and second members are assembled, the shaft 10 extends along axis A and goes successively through an opening 13A provided in a first lateral leg 13 of the second member 23, through an opening 14A provided in a central part 14 of the first member 13, and through an opening 15A provided in a second lateral leg 15 of the second member 23. The lateral legs 13, 15 of the second member 23 are located on each side of the central part 14 of the first member 13. All openings 13A, 14A, 15A are through holes. However, in other embodiments one or more of the openings 13A, 14A, 15A may be blind holes. Openings 13A and 15A have a circular cross-section of substantially the same size (i.e. substantially the same diameter) as that of the shaft 10. When the fixing device 1 is assembled, the shaft 10 is held by friction, welding, swaging, crimping, pressing, clamping or any other appropriate fixing solution inside the openings 13A, 15A, or otherwise attached to the legs 13, 15 of the second member 23. Opening 14A has an oblong cross-section with a close outline. The longitudinal direction LD of oblong opening 14A is perpendicular to axis A. The shaft 10 can turn inside the opening 14A and can move along the longitudinal direction LD of the opening 14A (see FIGS. 3-4: the position of the shaft 10 inside the opening 14A is different). Accordingly, with respect to the first member 13, the second member 23 is movable in rotation around the first axis A, while being movable in translation in a first direction D parallel to the longitudinal direction LD. In other embodiments, the oblong opening 14A may be curved or arcuate, thus allowing the shaft 10 to move in the oblong opening 14A in an arcuate path generally perpendicular to the axis A.

The fixing device 1 further comprises a flexible member 20 (shown in FIGS. 3-4, not depicted in FIGS. 1-2) passing through the main body 2—e.g. through the first member 1, through the passage 5 between the members 13, 23, and through the second member 23—and extending from the main body 2 to form a loop 20P around a bony structure (not shown in FIGS. 1-4). Here, the flexible member 20 has two end portions 20E and an intermediate portion forming said loop 20P. The loop 20P extends outside the main body 2 from a passage 21 provided in the first member 13, and the end portions 20E extend from the main body 2 from a passage 22 provided in the second member 23. The loop 20P is tightened or tensioned around a bony structure by pulling on the end portions 20E, and the flexible member 20 is locked in position by clamping the portions 13, 23 and thus pressing the flexible member 20 between the rod 4 and a surface of the first member 13.

In this example, there is only one exit passage 22 for the end portions 20E and one loop passage 21 for the loop 20P. However, in other examples, not shown, the main body 2 is provided with two exit passages, i.e. one for each end 20E of the flexible member 20. Similarly, the main body 2 may be provided with two loop passages, i.e. one for each branch of the loop 20P.

The main body 2 is further provided with a first passage 5 for receiving a portion 4A of the rod 4. The first passage 5 is defined by recesses provided in the inside faces of the first and second members 13, 23.

The exit passage 22 and the loop passage 21 both communicate with the first passage 5. In the appended figures, the exit passage 22 is located above the first passage 5 whereas the loop passage 21 is located below the first passage 5. When the flexible member 20 is passed through the main body 2 and the rod portion 4A is placed into the main body 2, between the members 13, 23, portions of the flexible member 20 (located between the end portions 20E and the loop 20P) are held between the rod portion 4A and the internal walls of the members 13, 23 defining the first passage 5.

In the example of FIGS. 1-4, the exit passage 22, the first passage 5, and the loop passage 21 are substantially aligned and the flexible member 20 passes on the same side of the rod 4, near the first axis A. In other examples, not shown, the flexible member 20 passes on each side of the rod 4, i.e., one branch of the flexible member 20 passes on one side of the rod 4, while the other branch of the flexible member 20 passes on the other side of the rod 4.

The fixing device 1 also comprises a clamping mechanism for bringing and maintaining the first and second members 13, 23 in a clamping position in which the rod 4 and the flexible member 20 are held tight.

Here, the clamping mechanism comprises a screw 6. The screw 6 has a shank 6B going through the first and second members 13, 23, and a head 6A having a profile (being internal or external) that allows the screw 6 to be driven in rotation. In more detail, the screw shank 6B passes through an orifice 9 provided in an engagement portion 123 of the second member 23, and can be screwed into a threaded hole 13 formed in an engagement portion 113 of the first member 13. The screw shank 6B is provided with an outside thread for engagement with the inside thread of the hole 13.

The orifice 9 is oblong, the longitudinal direction N (see FIG. 2) of this orifice 9 being oriented substantially perpendicular to the screw axis S and to the first axis A. Due to this oblong shape, the second member 23 is movable in translation in the longitudinal direction N with respect to the screw 6 (when the screw 6 is screwed into the first member 13).

The screw 6 and the engagement portions 113, 123 of the first and second members 13, 23 are located on the side of the main body 2 which is opposite to the hinge (i.e., to axis A), with respect to the rod 4.

By tightening the screw 6, the first and second members 13, 23 are moved toward each other and the rod portion 4A is clamped inside the first passage 5, between the first and second members 13, 23, while the flexible member 20 is simultaneously clamped between the rod portion 4A and the members 13, 23.

The screw head 6A has a generally spherical, convex or conical shape and the lower part of the screw head (i.e., the part close to the shank 6B) defines a first sloped or curved surface 31. When the screw 6 is tightened, the screw head 6A comes into abutment with a second sloped or curved surface 32 defined on the outside face of the engagement portion 123, around the orifice 9, and the screw head 6A pushes on the engagement portion 123. Thus, a force F (see FIG. 4) is exerted by the screw head 6A on the second member 23, through the first and second surfaces 31, 32. This force F has a component along the first direction D and, advantageously, the force F is aligned with the first direction D.

Figure 1:
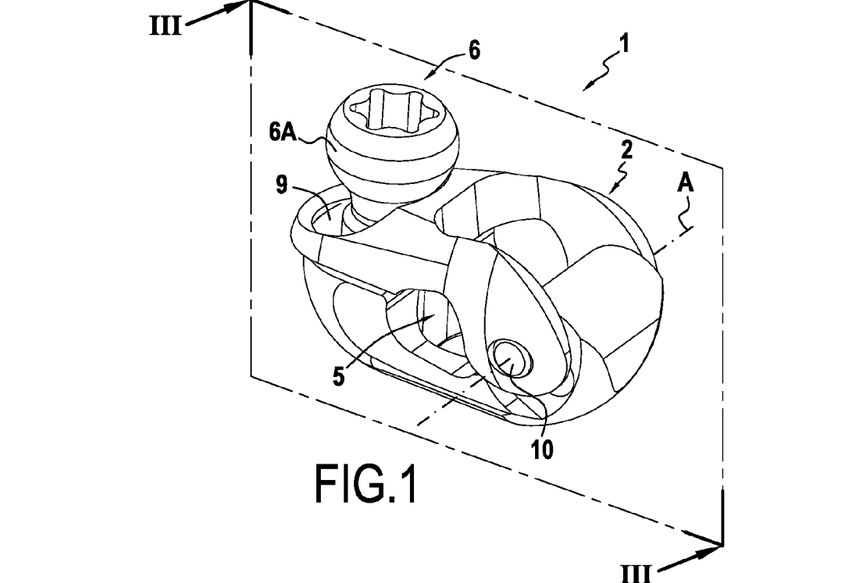
FIG. 1 is a perspective view of an example of a fixing device.
Figure 2:
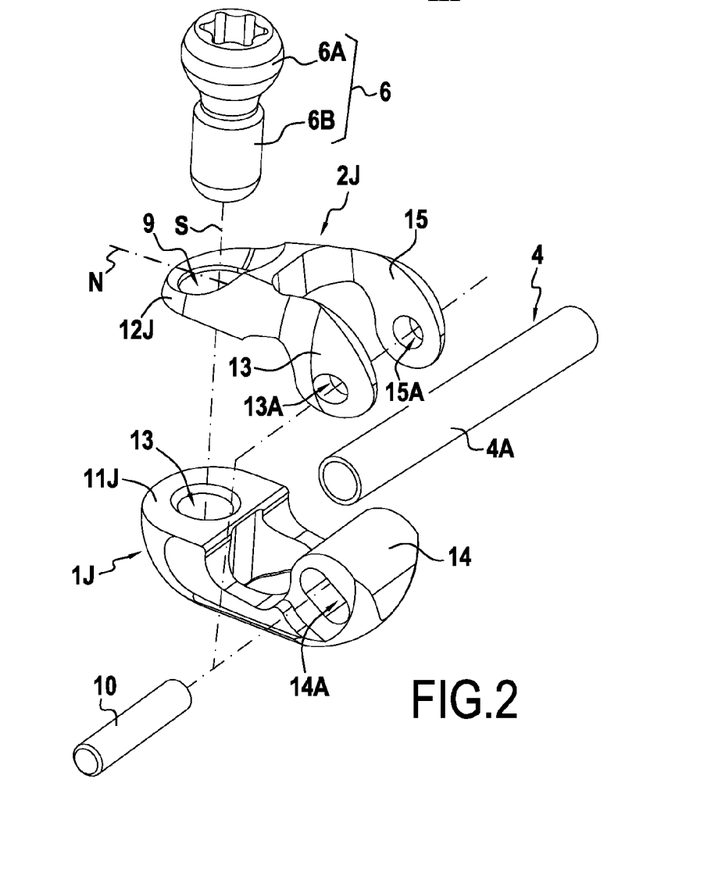
FIG. 2 is an exploded view of the fixing device of FIG. 1 with a support member.
Figure 3:
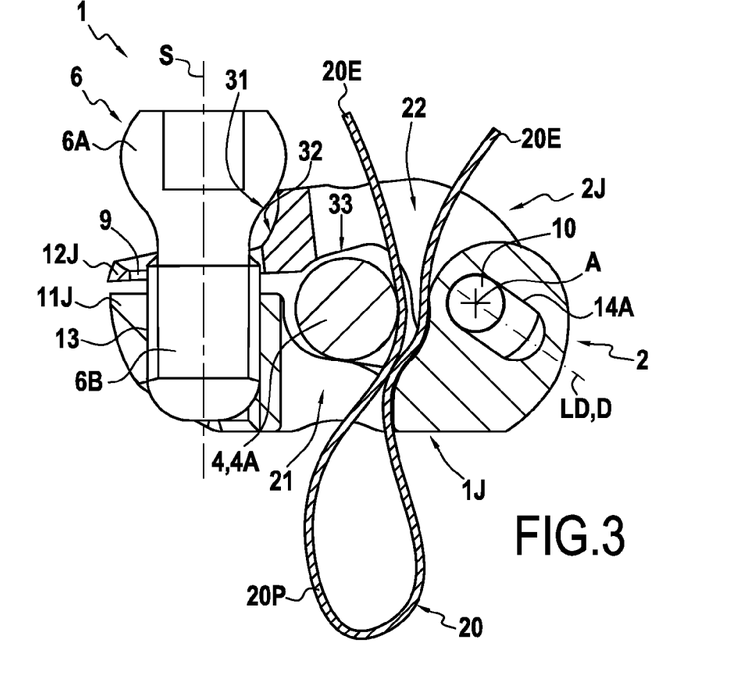
FIG. 3 is a sectional view of the fixing device of FIG. 1, along plane III-III.
Figure 4:
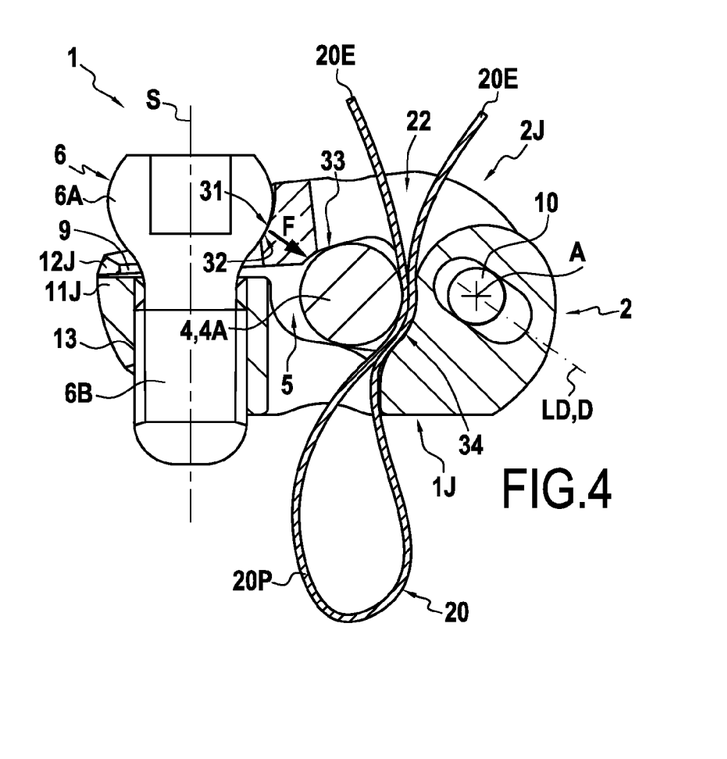
FIG. 4 is a sectional view, like that of FIG. 3, showing the fixing device in another position (a clamping position).

The tightening of the screw 6 makes the pivot shaft 10 move through the oblong opening 14A in the first direction D, as illustrated in FIGS. 3-4 (the device being shown in a non-clamping position in FIG. 3, and in a clamping position in FIG. 4). So, when the screw 6 is tightened, the second member 23 is moved in translation along the first direction D, with respect to the first member 13. The second member 23 has an internal face with an abutment face 33 for the rod 4, the abutment face 33 pushing the rod 4 towards the first member 13 when the second member 23 is moved relative to the first member 13. In turn, the rod 4 presses the portions of the flexible member 20 against the face 34 of the first member 13, thereby locking the flexible member 20 in position.

Figure 5:
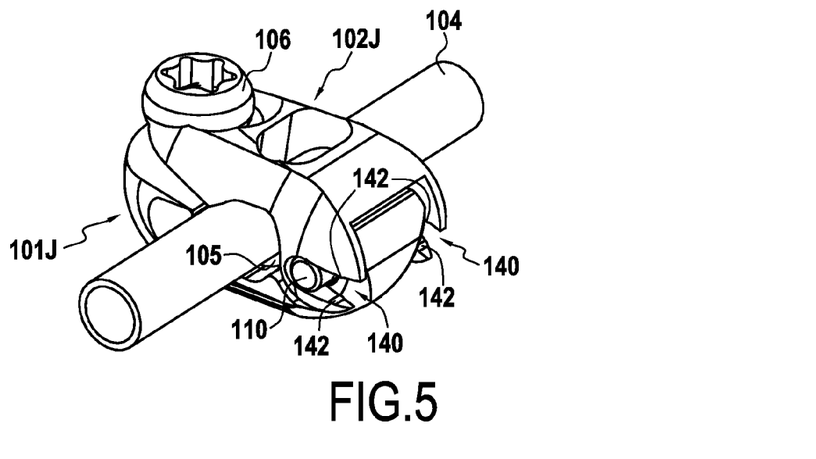
FIG. 5 is a perspective view of another example of a fixing device.
Figure 6:
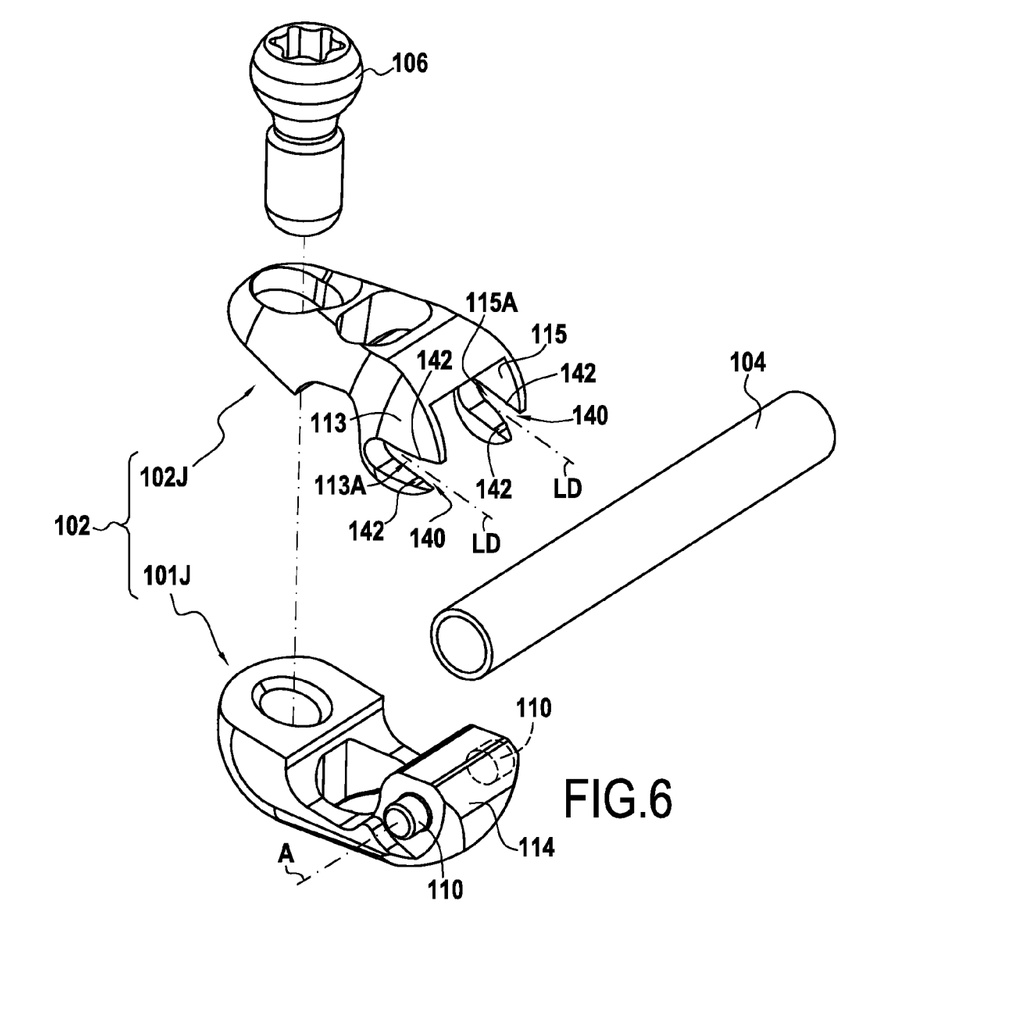
FIG. 6 is an exploded view of the fixing device of FIG. 5.

Another example of fixing device 101 is shown in FIGS. 5-6. This device differs from the one of FIGS. 1-3 by the hinge linking the first member 1013 with the second member 1023. The other parts are substantially the same and will not be described again, for the sake of conciseness.

In the example of FIGS. 5-6, the hinge between the first and second members 1013, 1023 comprises two pins 110 aligned with each other and both extending along axis A in opposite directions from the first member 1013. Those pins 110 extend from the lateral sides of the central part 114 of the first member 1013 and are respectively engaged through openings 113A, 115A respectively provided in first and second lateral legs 113, 115 of the second member 1023. The lateral legs 113, 115 of the second member 1023 are located on each side of the central part 114 of the first member 1013.

Openings 113A, 115A are oblong holes having a width corresponding substantially to the diameter of the pins 110. The longitudinal direction LD of each opening (see FIGS. 3-4) is parallel to the first direction D and is substantially perpendicular to the first axis A. Accordingly, the pins 110 are movable within the openings 113A, 115A both in rotation around their axis A and in translation in direction D. As a consequence, with respect to the first member 1013, the second member 1023 is movable in rotation around the first axis A, while being movable in translation in direction D, generally perpendicular to the axis A. In other embodiments, the oblong openings 113A, 115A may be curved or arcuate, thus allowing the pins 110 to move in the oblong openings 113A, 115A in an arcuate path generally perpendicular to the axis A.

In cross-section, the outline of each opening 113A, 115A is open, meaning that this outline has a gap 140 and that each opening 113A, 115A opens out at the gap 140. The gap 140 is provided at a longitudinal end of the oblong opening 113A, 115A. Thus, when assembling the first and second members 1013, 1023, the pins 110 are inserted into the openings 113A, 115A, through the gaps 140. Then, the screw 106 is mounted on the members 1013, 1023. When the screw 106 is in position but not tightened, the translational movement of the second member 1023 with respect to the first member 1013 is possible while being limited, and the pins 110 cannot exit the openings 113A, 115A, through the gap 140, because the length of the oblong openings 113A, 115A (i.e. their length along the longitudinal direction LD) is greater than the maximum length of possible translation of the second member 1023 along direction D.

When the screw 106 is not yet mounted on the members 1013, 1023, in order to impede the pins 110 from being removed from the openings 113A, 115A, small stops 142 protruding inside the opening 113A, 115A may be provided near the gap 140. To assemble the members 1013, 1023 together, the pins 110 are inserted in force into the openings 113A, 115A, past the stops 142. The pins 110 cannot go backward, past the stops 142, unless a sufficient force exceeding a threshold amount of force is exerted thereon.

Pins 110 may be made in one piece with the central part 114 of the first member 1013 or, alternatively, in separate pieces. In particular, pins 110 may be formed by the end portions of a shaft passing through the central part 114 and being fixedly linked thereto or by end portions of shafts extending from the part 114 in opposite directions.

FIG. 7 shows an example of a stabilization system for stabilizing at least two vertebrae V1, V2, the system comprising: a first fixing device configured to be fastened to a first vertebra V1, a second fixing device configured to be fastened to a second vertebra V2, and a support member—e.g. a rod 4—for connecting the first and second anchors together, thereby providing stabilization between the first and second vertebrae. The first and second fixing devices may be the same or different and may be devices 1, 101 such as those of FIGS. 1-6. In this example, the first and second fixing devices 1, 101 are respectively fastened to the laminae of the vertebrae V1, V2. FIG. 7 is diagrammatic and, in particular, the flexible members of the fixing devices 1, 101 are not shown.

The invention claimed is:

1. A fixing device for fixing a bony structure to a support member, the fixing device comprising:
   a main body comprising first and second members defining between them a first passage configured for receiving the support member, the second member including an oblong opening extending therethrough and the second member being pivotable with respect to the first member, around a first axis, and
   a clamping mechanism engaging the main body through the oblong opening extending through the second member and being configured to move the first and second members towards each other for clamping the support member therebetween through rotation of the clamping mechanism about a rotational axis,
   wherein the first axis is movable in translation along a first direction so that the second member is movable in translation along the first direction, with respect to the first member,
   wherein as the clamping mechanism is inserted through the oblong opening to engage the main body, a surface of the clamping mechanism engages a surface of the second member to translate the second member relative to the first member along the first direction transverse to the rotational axis so as to narrow the first passage; and
   wherein the fixing device is adapted to receive a flexible member within the first passage, in a direction transverse to a longitudinal axis of the first passage, the fixing device being adapted to clamp the flexible member between at least one of the first and second members and the support member, when a support member is disposed within the first passage.

2. The fixing device of claim 1, wherein the clamping mechanism comprises a clamping member which is configured to cooperate with the first and second members so as to exert a force on the second member, the force having a component along the first direction, and wherein the resultant force exerted by the clamping member on the second member is oriented substantially along the first direction.

3. The fixing device of claim 2, wherein the clamping member is a screw with a screw head and a shank, the shank being threadably engaged with the first member and the screw head being configured to exert said force on the second member when the screw is tightened.

4. The fixing device of claim 3, wherein the surface of the clamping mechanism is a first sloped or curved surface defined by the screw head, and wherein the surface of the second member is a second sloped or curved surface defined by an outside face of the second member, said force being exerted through the first and second surfaces when the screw is tightened.

5. The fixing device of claim 1, wherein one of the first and second members is provided with a pivot shaft extending along the first axis, and wherein the other one of the first and second members is provided with at least one oblong opening through which the pivot shaft passes, the oblong opening through which the pivot shaft passes having a longitudinal direction substantially parallel to the first direction.

6. The fixing device of claim 5, wherein the pivot shaft is a one-piece shaft extending through the first and second members.

7. The fixing device of claim 5, wherein the pivot shaft is defined by two pins protruding from one member, on opposite sides thereof, and extending through the oblong openings of the other member.

8. The fixing device of claim 5, wherein the oblong opening through which the pivot shaft passes is open in its longitudinal direction.

9. The fixing device of claim 1, wherein the second member has an inside face defining an abutment for engagement against the support member, the abutment pushing the support member towards the first member when the second member is moved in translation in the first direction.

10. The fixing device of claim 1, wherein a pivoting mechanism is provided between the first and second members, the pivoting mechanism comprising a pivot shaft being received in an oblong opening provided in at least one of the first and second members.

11. A system comprising at least one support member, at least one fixing device according to claim 1, for fixing a bony structure to the support member, and a flexible member passing through the first passage, between the support member and said first and/or second member, and extending beyond the main body for attachment to the bony structure.

12. A system for stabilizing at least two vertebrae, the system comprising:
   a first fixing device configured to be fastened to a first vertebra,
   a second fixing device configured to be fastened to a second vertebra, and
   a support member, more particularly a rod, for connecting the first and second devices together, thereby providing stabilization between the first and second vertebrae,
   wherein at least the first fixing device is a fixing device according to claim 1.

13. A method for connecting a bony structure to a support member, comprising the steps of:
   providing a system according to claim 11,
   passing the flexible member around the bony structure and tensioning said flexible member, and
   impeding movement of the bony structure relative to the support member by fixing the position of the flexible member and support member relative to the fixing device.

14. A method for stabilizing at least two vertebrae, comprising the steps of:
   providing a system according to claim 12,
   fixing the first fixing device to a first vertebra,
   fixing the second fixing device to a second vertebra, and
   impeding relative movement between the first and second fixing devices by connecting each of them to the support member, relative movement between the first vertebra and the support member being impeded by fixing the position of the flexible member and support member relative to the first fixing device.

* * * * *